United States Patent [19]

Jons et al.

[11] Patent Number: 5,783,452

[45] Date of Patent: Jul. 21, 1998

[54] COVERED MICROCHANNELS AND THE MICROFABRICATION THEREOF

[75] Inventors: Steve D. Jons; Paul J. O'Connor; Ing-Fen Hu, all of Midland, Mich.

[73] Assignee: University of Washington, Seattle, Wash.

[21] Appl. No.: 595,683

[22] Filed: Feb. 2, 1996

[51] Int. Cl.⁶ .......................... G01N 33/00; G01N 30/02; G03C 5/00

[52] U.S. Cl. .......................... 436/183; 436/161; 422/89; 422/70; 430/312

[58] Field of Search .......................... 427/489; 430/312, 430/272.1; 436/161, 183; 422/89, 70

[56] References Cited

U.S. PATENT DOCUMENTS

| | | | |
|---|---|---|---|
| 3,615,913 | 10/1971 | Shaw | 148/33.3 |
| 3,895,429 | 7/1975 | Huang et al. | 29/580 |
| 5,116,495 | 5/1992 | Prohaska | 210/198.2 |
| 5,128,737 | 7/1992 | Van Der Have | 357/40 |
| 5,205,902 | 4/1993 | Horton et al. | 156/643 |
| 5,298,587 | 3/1994 | Hu et al. | 528/10 |
| 5,320,875 | 6/1994 | Hu et al. | 427/493 |
| 5,575,929 | 11/1996 | Yu et al. | 216/10 |

OTHER PUBLICATIONS

Manz et al., *Journal of Chromatography*, vol. 593, pp. 253–258 (1992).
Wilson, C. Grant, *Intro. to Microlithography*, 2nd Ed., pp. 139–267 (1994).

*Primary Examiner*—Janet C. Baxter
*Assistant Examiner*—Rosemary Ashton
*Attorney, Agent, or Firm*—Christensen, O'Connor, Johnson & Kindness PLLC

[57] ABSTRACT

The present invention is a covered microchannel comprising: a) a substrate; b) an etched material adhered to the substrate; and c) a silicon-carbon material adhered to the etched material in such a manner to form a covered microchannel; wherein the silicon-carbon material comprises $SiO_{1.8-2.4}$ $C_{0.3-1.0}$ and $H_{0.7-4.0}$ containing at least one of the following functional groups:

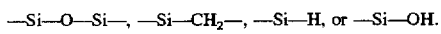

$-Si-O-Si-$, $-Si-CH_2-$, $-Si-H$, or $-Si-OH$.

The covered microchannel can be prepared by the steps of: a) coating a filler material onto a substrate having a groove, wherein the filler material covering the substrate fills the groove; b) removing filler material from the substrate but not from the groove; c) coating the substrate and the filler with an adhering, formable, capping material; and d) removing the filler from the groove. An etched laminate can also be used to prepare the covered microchannel.

The present invention provides a covered microchannel that can be prepared under milder conditions than those previously contemplated, thereby allowing greater flexibility in the choice of material of the substrate. The covered microchannel can be used, for example, in micro-liquid or micro-gas chromatographic or electrophoretic applications.

8 Claims, 2 Drawing Sheets

COVERED MICROCHANNELS AND THE MICROFABRICATION THEREOF

BACKGROUND OF THE INVENTION

This invention relates to covered microchannels, which are useful in chromatographic and electrophoretic applications.

Miniaturization of separation devices such as liquid or gas chromatographs is desirable because of reduced loadings and solvent consumption. Theoretically, open tubular chromatography can provide an order of magnitude efficiency improvement over conventional packed column chromatography, particularly for a column having an inner diameter around the order of 10 microns. According to Manz et al., in *Journal of Chromatography*, Vol. 593, p. 253 (1992), "[d]eviations from theoretical predictions have usually been caused by inhomogeneity in column packings or capillary diameters, inappropriate injections or large detection volumes." Accordingly, Manz et al. developed a technique for the manufacture of silicon-etched microchannel systems using the steps of film deposition, photolithography, etching, and bonding applied to a polished silicon wafer. The microchannel is capped (covered) by the bonding step, which generally requires temperatures on the order of 400° C. and voltages on the order of 500 V. Inasmuch as this requirement restricts the kind of substrate that can be used to prepare the covered microchannel, it would be desirable to provide a way to cap the etched substrate using milder conditions.

SUMMARY OF THE INVENTION

The present invention is a method of preparing a covered microchannel comprising the steps of: a) coating a filler material onto a laminate which comprises a substrate having adhered thereto an etchable material having a groove, so that the filler material covers the etchable material and fills the groove; b) removing filler material from the etchable material but not from the groove; c) coating the etchable material and the filler material remaining in the groove with an adhering, formable, capping material; and d) removing the filler from the groove.

In another aspect, the present invention is a method of preparing a covered microchannel comprising the steps of: a) coating a filler material onto a substrate having a groove, wherein the filler material covers the substrate and fills the groove; b) removing filler material from the substrate but not from the groove; c) coating the substrate and the filler with an adhering, formable, capping material; and d) removing the filler from the groove.

In another aspect, the present invention is a covered microchannel comprising: a) a substrate; b) an etched material adhered to the substrate; and c) a silicon-carbon material adhered to the etched material in such a manner to form a covered microchannel; the silicon-carbon material comprising $SiO_{1.8-2.4}$ $C_{0.3-1.0}$ and $H_{0.7-4.0}$ containing at least one of the following functional groups:

—Si—O—Si—, —Si—$CH_2$—, —Si—H, or —Si—OH.

In another aspect, the present invention is a covered microchannel comprising: a) an etched substrate; and b) a silicon-carbon material adhered to the etched substrate in such a manner to form a covered microchannel; the silicon-carbon material comprising $SiO_{1.8-2.4}$ $C_{0.3-1.0}$ and $H_{0.7-4.0}$ containing at least one of the following functional groups:

—Si—O—Si—, —Si—$CH_2$—, —Si—H, or —Si—OH.

The various aspects of the present invention address a need in the art by providing covered microchannels that can be prepared under conditions that are less stringent than those previously contemplated, thereby allowing greater flexibility in the choice of material of the substrate. The covered microchannel can be used, for example, in microliquid or micro-gas chromatographic or electrophoretic applications.

DETAILED DESCRIPTION OF THE INVENTION

Figure 1:
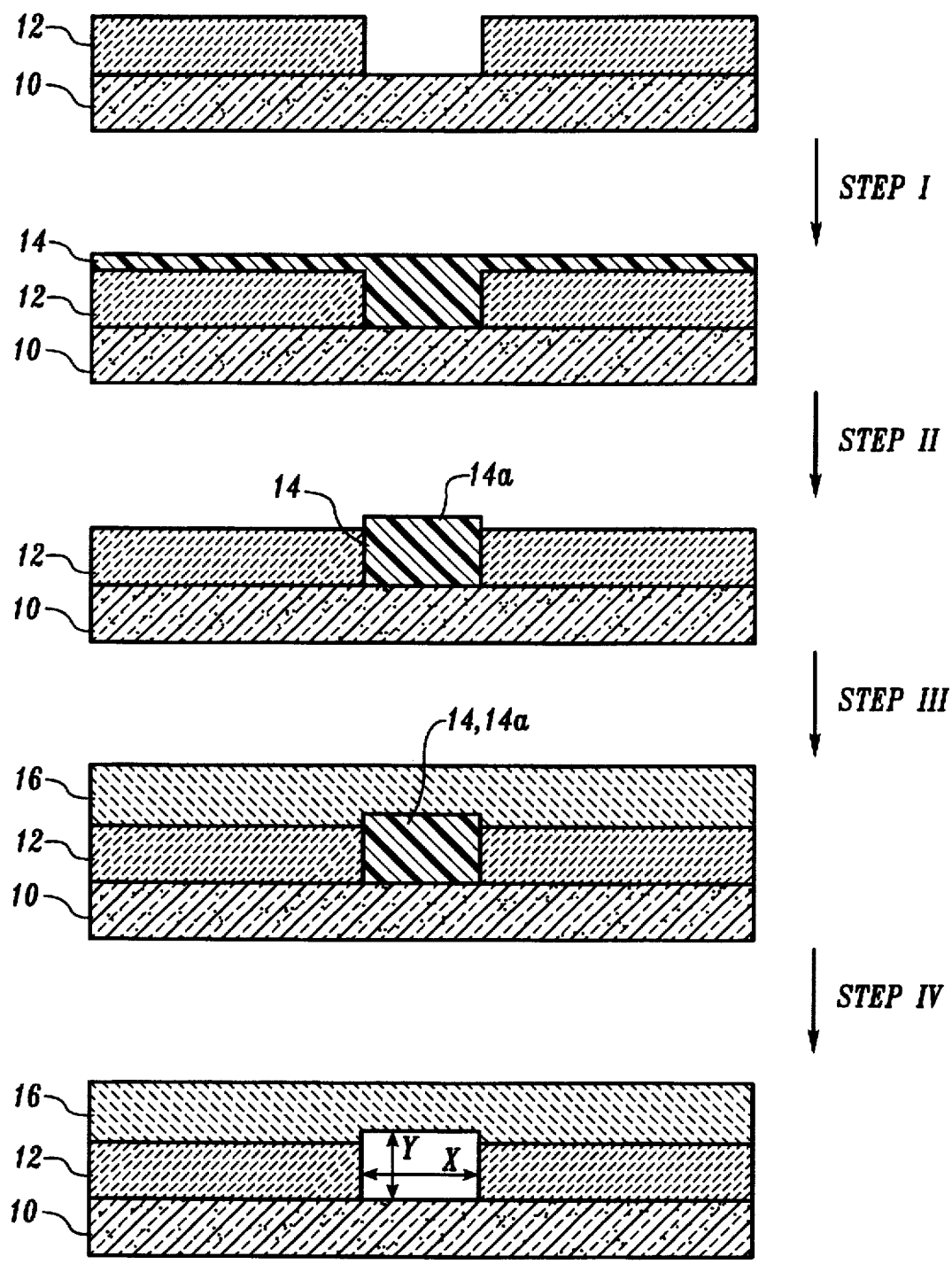
FIG. 1 is a sideview illustration of the steps used to prepare a covered microchannel in a preferred method.

A preferred method of preparing the covered microchannel of the present invention is illustrated in FIG. 1. In Step I of the method, a laminate (i.e., an uncovered microchannel), which is a substrate (10) having adhered thereto an etchable material having a groove (12), is coated with a photoactive material (14), which covers the etchable material (12) and fills the groove. In Step II, the photoactive material is patterned and developed so that all of the photoactive material is removed from the etchable material (12), except that which fills the groove. A lip (14a), which may form above the surface of the etchable material (12) after development of the photoactive material, can be minimized by spin coating at higher speeds, or using a less viscous photoactive material, or a combination of both. In Step III, the laminate with the filled groove is coated with an adhering formable, capping material (16), which is preferably a silicon-carbon material that is applied using plasma enhanced chemical vapor deposition (PECVD). In Step IV, the photoactive material (14, 14a) is removed by placing the now covered microchannel into a solvent for the photoactive material, such as acetone. The covered microchannel has a width and a height (depicted by the letters x and y, respectively, in the covered microchannel of FIG. 1) that is application dependent. Preferably, the width and height of the covered microchannel are each independently less than 500 microns. More preferably, the width and height are each independently less than about 100 microns, most preferably less than about 50 microns. More preferably, the width and height are each independently not less than about 1 micron, most preferably, not less than about 5 microns.

Figure 2:
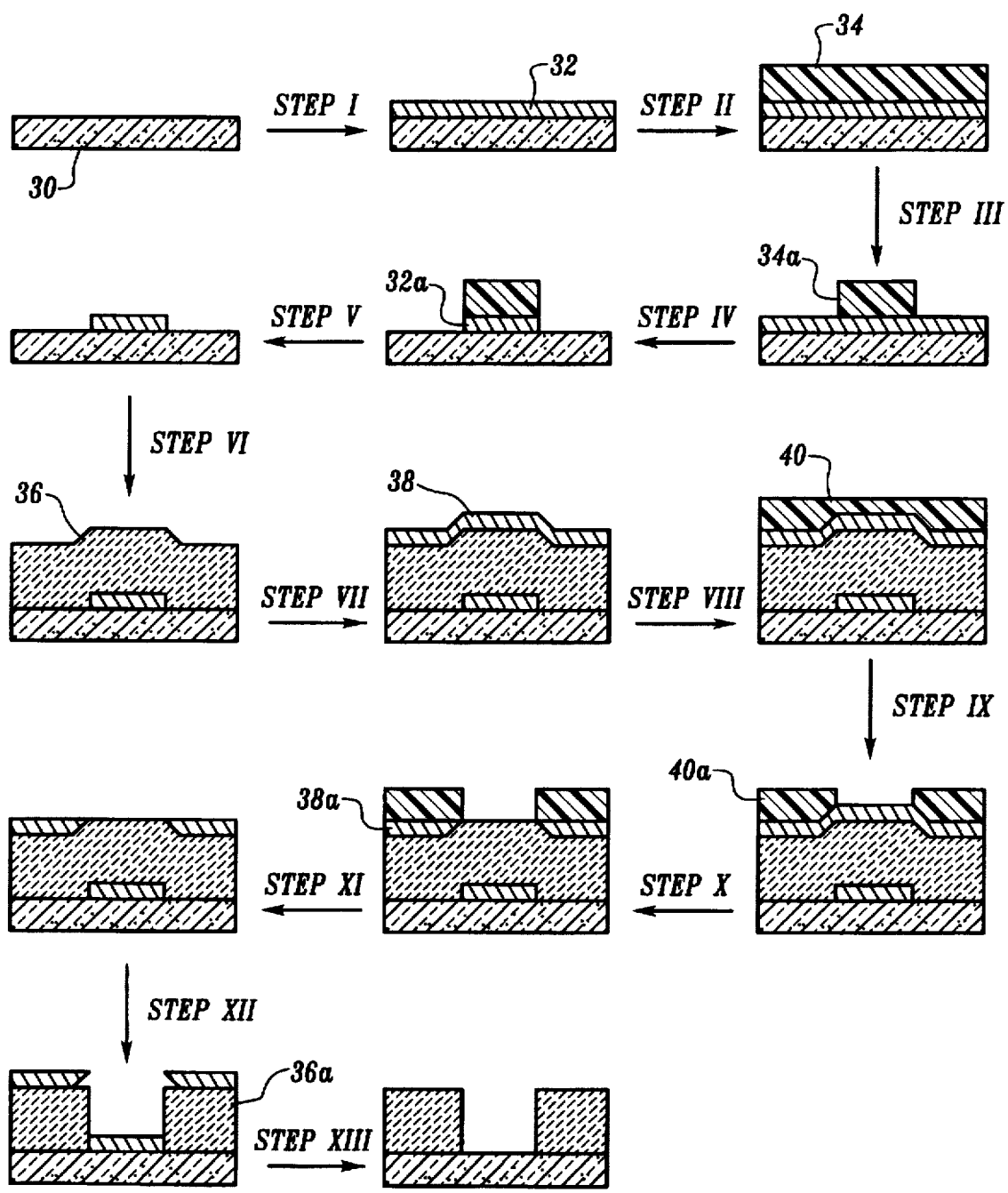
FIG. 2 is a sideview illustration of a preferred series of steps used to prepare the uncovered microchannel from which a preferred covered microchannel of FIG. 2 can be prepared.

The covered microchannel can be prepared from an uncovered microchannel, which can be prepared by any suitable method including those disclosed in the prior art, for example, Manz et al., supra. The covered microchannel can be prepared from an etched substrate, or from a laminate which comprises an etched material adhering to the substrate. Preparing a covered microchannel from the laminate is preferable, particularly when control of the depth of the groove (etch) is desirable. Such control of depth can be achieved by insertion of a metal etch stop in the laminating process as illustrated in the steps shown in FIG. 2. Referring now to FIG. 2, in Step I, a substrate (30) is first coated with a first metal layer (32). The first metal layer (32) is coated with a photoactive material (34) in Step II. In Step III, the photoactive material (34) is patterned and developed so that all the photoactive material is removed except that portion which forms a pattern for the groove (34a). In Step IV, that portion of the first metal layer (32) that is not covered by the remaining photoactive material (34) is then removed, and in Step V, the remainder of the photoactive material (34a) is removed, leaving a substrate with a metal etch stop (32a) that forms a pattern for the groove.

In Step VI, a formable, etchable material (36) is deposited onto the substrate (30) and over the metal etch stop (32a), whereupon in Step VII a second metal layer (38) is deposited onto the formable, etchable material (36). A second photoactive material (40) is then applied to the surface of the second metal layer (38) in Step VIII. In Step IX, the second photoactive material (40) is patterned and developed in such a manner that the portion of the second photoactive material (40) which superposes and parallels the metal etch stop (32a) is removed, thereby exposing the portion of the second metal layer (38) that superposes and parallels the metal etch stop (32a).

In Step X, the portion of the second metal layer (38) that is not covered by the remainder of the second photoactive material (40a) as a result of the patterning step is removed so that only the region of formable, etchable material (36) that parallels the metal etch stop (32a) is not covered by the remainder of the second metal layer (38a). In Step XI, the remainder of the second photoactive material (40a) is removed. In Step XII, the formable, etchable material (36) that is not covered by the remainder of the second metal layer (38a) is etched down to the metal etch stop (32a). In Step XIII, the remainder of the second metal layer (38a) and the metal etch stop (32a) is removed to form an uncovered microchannel comprising the substrate (30) superposed by etched material (36a).

The composition of the substrate is not limited by resistance to the harsh conditions generally required for the fabrication of covered microchannels, since the covered microchannel can be prepared under comparatively mild conditions, that is, temperatures typically not greater than 150° C. The substrate can be organic, inorganic, or metallic. Examples of organic materials include resins such as epoxy resins; acrylic resins; unsaturated polyester resins; polyurethane resins; polycarbonate resins such as those prepared from bisphenol A or bishydroxyphenyl fluorene or combinations thereof; diglycol dialkyl carbonate resins, polyimide resins, melamine resins, phenolic resins, urea resins, and benzocyclobutene resins such as divinylsiloxane-bis-benzocyclobutene.

Examples of suitable inorganic materials for the substrate include silicon, silicon oxides, polysilanes, and polysiloxanes. Suitable metals are those that are capable of being laminated by electroplating, vapor deposition or sputtering. Examples of suitable metals include copper, silver, gold, nickel, chromium, tin, lead, zinc, aluminum, and titanium.

A formable, etchable material is preferably deposited onto the substrate to form a laminate. This laminate can then be processed as described herein to form a covered microchannel. The formable, etchable material is etched (grooved) to a depth and width that is appropriate for the desired application. For a micro-liquid or micro-gas chromatographic, or an electrophoretic application, grooves on the order of less than 100 microns wide and less than 100 microns deep are typical. The formable, etchable material is a material that can be applied to the substrate by vapor deposition or spin coating and is capable of being etched, particularly by plasma etching. The formable, etchable material is preferably silicon, a silicon oxide, or a silicon-carbon material that can be applied to the substrate by plasma enhanced chemical vapor deposition. More preferably, the formable, etchable material is a polymer of $SiO_{1.8-2.4}$ $C_{0.3-1.0}$ and $H_{0.7-4.0}$ containing at least one of the following functional groups:

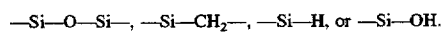

Examples of metals suitable for the preparation of the metal layers in the process of preparing the microchannels include copper, silver, gold, nickel, chromium, tin, lead, zinc, aluminum, and titanium. Copper and aluminum are particularly preferred.

The filler material is any material that can fill the groove of the etched substrate, and that can subsequently be removed after the substrate is capped with an adhering, formable, capping material. Examples of suitable filler materials include waxes, metals such as those disclosed for use in the preparation of the etched substrate, and photoactive materials. When a wax or a metal is used as a filler material, the process for preparing the covered microchannel is somewhat different than that described for a photoactive filler material.

When wax is used as a filler material, the wax is advantageously dissolved in a solvent and spun onto the etched substrate. The wax can then be polished off the substrate, leaving only the groove filled. The adhering, formable, capping material can then be applied, and the wax can be melted away, dissolved in a suitable solvent, or sublimed, leaving a covered microchannel.

Metal can be used as a filler material by electroplating from the metal etch stop which is exposed at Step XII of FIG. 2. In a first step, a metal, which is preferably, but not necessarily, the same as the metal used to form the metal etch stop, can be electroplated from the metal etch stop to fill the groove. The metal that remains on top of the substrate after Step XII (referred to as 38a in FIG. 2) can then be removed by a quick acid etch without substantially depleting metal from the filled groove. The adhering, formable, capping material can then be applied, and the metal in the groove can be removed by reversing the plating potentials.

The preferred filler material is a photoactive material, also known as photoresist. The photoresist may be positive resist or negative resist such as those known in the art. (See, for example, C. Grant Willson in *Introduction to Microlithography*, Second Edition. Chapter 3, L. F. Thompson et al., Eds.; American Chemical Society, Washington, D.C., pp. 139–267 (1994).

An adhering, formable, capping material is a material that can be applied to the substrate in a preformed state, then formed into a solid state. Such materials include curable resins such as those described hereinabove; metals capable of being laminated by electroplating, vapor deposition or sputtering such as those described hereinabove; and silicon-carbon compounds deposited onto the substrate by plasma-enhanced chemical vapor deposition.

The adhering, formable, capping material preferably comprises a $SiO_{1.8-2.4}$ $C_{0.3-1.0}$ and $H_{0.7-4.0}$ containing at least one of the following functional groups:

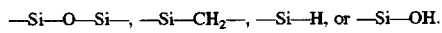

This preferred silicon-carbon material is formable by plasma-enhanced chemical vapor deposition of an organo-silicone monomer gas in a plasma reaction zone and oxygen gas, as disclosed by Hu et al. in U.S. Pat. Nos. 5,298,587 and 5,320,875, incorporated herein by reference. The organosilicone monomer is advantageously plasma polymerized in the presence of excess oxygen using a power density within the range of about $10^6$ to about $10^8$ J/Kg in the presence of the substrate. Examples of organosilicone compounds include silanes, siloxanes, and silazanes, and combinations thereof. Examples of silanes include dimethoxydimethylsilane, methyltrimethoxysilane, tetramethoxysilane, methyltriethoxysilane, diethoxydimethylsilane, methyltriethoxysilane, triethoxyvinylsilane, tetraethoxysilane, dimethoxymethylphenylsilane, phenyltrimethoxysilane, 3-glycidoxypropyl-trimethoxysilane, 3-methacryloxypropyl-trimethoxysilane, diethoxymethylphenylsilane, tris(2-methoxyethoxy) vinylsilane, phenyltriethoxysilane, and dimethoxydiphenylsilane. Examples of siloxanes include tetramethyldisiloxane (TMDSO) and hexamethyldisiloxane. Examples of silazanes include hexamethylsilazane and tetramethylsilazane.

The preferred plasma enhanced chemical vapor deposited silicon-carbon material exhibits excellect adhesion to a variety of substrates including silicon, silicon dioxide, metals, and polymers.

The following example is for illustrative purposes only and is not intended to limit the scope of this invention. The Roman numerals are used for convenience and refer to the steps of FIG. 2.

EXAMPLE

Preparation of a Covered Microchannel

A 4" diameter, 1/16" thick transparent silicon-oxide disc (manufactured by ESCO Products) was prepared for metallizing by cleaning in an oxygen plasma for 30 minutes. The wafer was then rinsed in water and dried in a spinner. A 2000-Å layer of aluminum was sputtered onto the cleaned disc (Step I). Four microns of photoresist (Shipley, S1400-37) were then spin coated onto the metal by applying a photoresist puddle over the wafer and spinning the wafer at 500 rpm for 30 seconds, followed by spinning at 2700 rpm for 30 seconds (Step II). The edge bead that formed was removed by acetone in the last 10 seconds of spinning. The solvent was driven off by a soft bake at 100° C.

The photoresist was masked and developed, and then removed from all areas except those corresponding with the intended column regions and alignment marks (Step III). The aluminum layer was removed in the exposed areas by a phosphoric acid etching bath (Step IV). The remainder of the photoresist was then removed by acetone and methanol rinses of the disc while it was being spun on the spin coater (Step V). The result was a 2000-Å thick, 10-micron wide metal etch stop layer that covered the substrate in the column regions.

Approximately 10 microns of silicon-carbon material was deposited on the substrate and over the metal etch stop by PECVD using flow rates of 30 sccm of oxygen and 5 sccm of tetramethyldisiloxane, and a coating power of 150 Watts (Step VI). The silicon-carbon material layer composition was approximately $SiO_{1.8-2.4}$ $C_{0.3-1.0}$ and $H_{0.7-4.0}$. A 2000-Å layer of aluminum was sputtered onto the coated disc (Step VII). Photoresist was applied as before (Step VIII), except that the development and subsequent removal of photoresist corresponded to the region of metal that superposed and paralleled the metal etch stop (Step IX). The exposed metal was removed by phosphoric acid etching (Step X) and the remainder of the photoresist was then removed to produce an exposed area of the silicon-carbon material that superposed and paralleled the metal etch stop (Step XI).

The exposed silicon-carbon material was plasma etched down to the metal etch stop using oxygen and $CF_4$ (Step XII). The remainder of the metal was removed by rinsing in a phosphoric acid bath for several hours (Step XIII), leaving a wafer with a pattern of grooves that were 10 microns wide and 10 microns deep.

Photoresist was spin coated over the grooved wafer using a 1500 rpm spin velocity. The photoresist was masked and developed, and all of the photoresist except that which filled the grooves was removed. A lip of photoresist above the surface of the silicon-carbon material remained as a result of planarization. The wafer with the filled grooves was coated with about 15 microns of silicon-carbon material by PECVD, as described heretofore. Holes were drilled through the cap at two ends of the microchannel to expose the photoresist fill material. Photoresist was removed by sonicating the covered wafer in an acetone bath to produce the covered microchannel.

What is claimed is:

1. A method of preparing a covered microchannel comprising the steps of:
   a) coating a filler material onto a laminate which comprises a substrate having adhered thereto an etchable material having a groove, so that the filler material covers the etchable material and fills the groove;
   b) removing filler material from the etchable material but not from the groove;
   c) coating the etchable material and the filler material remaining in the groove with an adhering, formable, capping material to form a capped laminate;
   d) uncovering the filler material that remains in the groove at both ends of the groove; and
   e) removing the filler from the groove with a solvent for the filler, so that the capping material and the etchable material form the covered microchannel.

2. The method of claim 1 wherein in step (a), the filler material is a photoactive material or a wax.

3. The method of claim 2 wherein the filler material is a photoactive material.

4. The method of claim 2 wherein in step (c), the adhering, formable, capping material is a resin; a metal capable of being laminated by electroplating, vapor deposition or sputtering; or an organosilicone compound deposited onto the substrate by plasma-enhanced chemical vapor deposition.

5. The method of claim 4 wherein the adhering, formable, capping material is an epoxy resin, an acrylic resin, an unsaturated polyester resin, a polyurethane resin, a diglycol dialkyl carbonate resin, a polyimide resin, a melamine resin, a phenolic resin, a urea resin, or a benzocyclobutene resin.

6. The method of claim 4 wherein the adhering, formable, capping material is copper, silver, gold, nickel, chromium, tin, lead, zinc, aluminum, or titanium.

7. The method of claim 6 wherein the adhering, formable, capping material is copper or aluminum.

8. The method of claim 4 wherein the adhering, formable, capping material comprises a silicon-carbon material of $SiO_{1.8-2.4}$ $C_{0.3-1.0}$ and $H_{0.7-4.0}$ containing at least one of the following functional groups:

—Si—O—Si—, —Si—CH$_2$—, —Si—H, or —Si—OH.

* * * * *